United States Patent [19]
Radlowski et al.

[11] Patent Number: 5,095,156
[45] Date of Patent: Mar. 10, 1992

[54] CATALYZED VAPOR PHASE PROCESS FOR MAKING ALCOHOLS

[75] Inventors: Cecelia A. Radlowski, Riverside; Gary P. Hagen, Glen Ellyn, both of Ill.

[73] Assignee: Amoco Corporation, Chicago, Ill.

[21] Appl. No.: 702,837

[22] Filed: May 20, 1991

Related U.S. Application Data

[63] Continuation of Ser. No. 413,314, Sep. 27, 1989, abandoned.

[51] Int. Cl.$^5$ ............................................. C07C 29/34
[52] U.S. Cl. ....................................... 568/905; 568/697; 568/902.2; 585/639
[58] Field of Search ............................................ 568/905

[56] References Cited

U.S. PATENT DOCUMENTS

| | | | |
|---|---|---|---|
| 1,755,692 | 4/1930 | Herrman et al. | 260/156 |
| 1,992,480 | 2/1935 | Fuchs et al. | 260/156 |
| 2,050,788 | 8/1936 | Fuchs et al. | 260/156 |
| 2,861,110 | 11/1958 | Herzenberg et al. | 260/642 |
| 3,328,470 | 6/1967 | Poe et al. | 260/642 |

FOREIGN PATENT DOCUMENTS

| | | |
|---|---|---|
| 336811 | 10/1930 | United Kingdom . |
| 478141 | 1/1938 | United Kingdom . |
| 2123411 | 6/1983 | United Kingdom . |

OTHER PUBLICATIONS

Pratt and Kubler, J. Org. Chem. 22, 540-2 (1957).
Dvornikoff and Farrar, J. Mol. Catalysis 33, 15–21 (1985).
Burk, Pruett and Campo, J. Am. Chem. Soc. 76, 52–56 (1954).

*Primary Examiner*—J. E. Evans
*Attorney, Agent, or Firm*—Reed F. Riley; William H. Magidson; Ralph C. Medhurst

[57] ABSTRACT

A catalyzed, continuous vapor phase process to convert a $C_2$ or higher alcohol and, optionally, one or more $C_1$ or higher alcohols, for example methanol and ethanol, to a mixture containing at least one higher molecular weight alcohol, for example, isobutanol, over a catalyst which is essentially magnesium oxide. The process also may have a lower aldehyde and/or ketone in the feed.

11 Claims, 1 Drawing Sheet

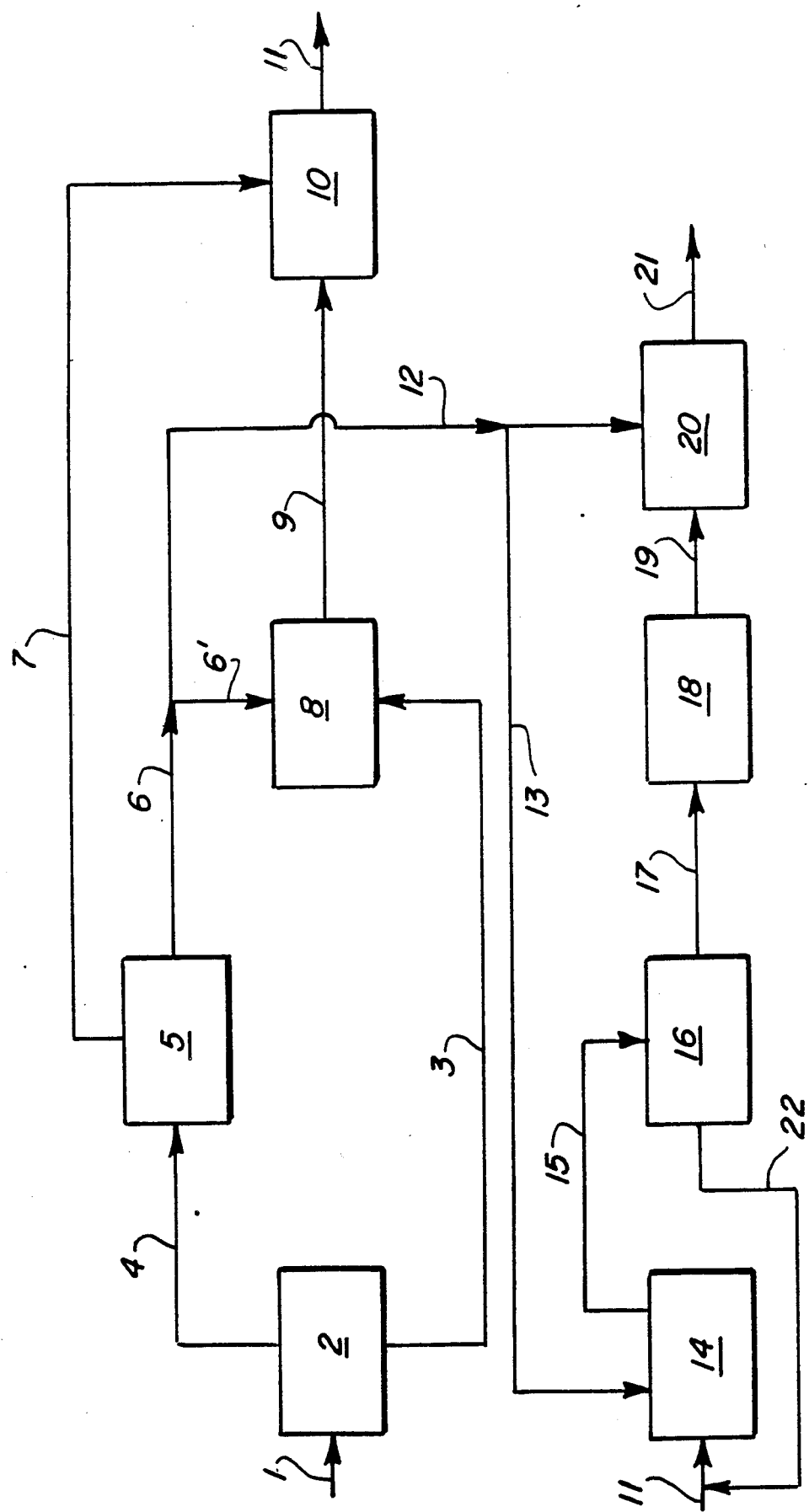

CATALYZED VAPOR PHASE PROCESS FOR MAKING ALCOHOLS

This is a continuation of application Ser. No. 413,314, filed Sept. 27, 1989, and now abandoned.

BACKGROUND OF THE INVENTION

This invention relates to a vapor phase process for catalytically converting one or more lower molecular weight alcohols, optionally in combination with a lower molecular weight aldehyde and/or ether, to a mixture containing at least one higher molecular weight alcohol over an alkaline catalyst and, more particularly, to a vapor phase, continuous process for converting a $C_2$ or higher alcohol, which may be in combination with one or more additional $C_1$ or higher alcohols, and optionally, an aldehyde and/or ether to a mixture containing at least one higher molecular weight alcohol over a catalyst which is essentially magnesium oxide.

In recent years there has been an upsurge in interest in the production of both chemicals and transportation fuels from non-petroleum carbon sources such as methane, tar sands, oil shale and the like. This interest has focused for lack of good direct conversion processes on indirect processes, which often go through a synthesis gas intermediate with subsequent conversion of the synthesis gas via Fisher-Tropsch and related processes to hydrocarbons and/or oxygenates. Oxygenates, particularly lower alcohols, are common products of such synthesis gas reactions, and high conversion, selective processes to convert an alcohol or a mixture of alcohols to higher molecular weight alcohols have substantial commercial potential.

One potential process uses the well-known, non-catalytic Guerbet reaction which converts a lower molecular weight alcohol to a branched or linear higher molecular weight alcohol in the presence of an alkali metal alkoxide dissolved in the alcohol to be converted. Such processes are uncatalysed, moderate temperature batch reactions. When considered for industrial use, however, the Guerbet reaction suffers an economic disadvantage in that a portion of the starting alcohol (and possibly some of the product) is consumed by oxidation to the corresponding carboxylic acid unless special agents are added. One publication suggests the use of a mixture of potassium hydroxide and boric oxide to suppress acid formation which is said to improve the yield.

More recently, an improved Guerbet reaction has been reported which uses a "catalyst" system employing magnesium oxide, potassium carbonate, and copper chromite for converting, for example, ethanol to higher alcohols including 1-butanol, and 1-butanol to higher alcohols including 2-ethyl-1-hexanol (J. Org. Chem. 22, 540-2 (1957)). The reaction is of the batch type and the "catalyst" is said to have limited lifetime.

Another improvement in the Guerbet reaction, discussed in J. Mol. Catalysis 33, 15-21 (1985), uses a sodium alkoxide mixed with 5% rhodium on alumina as a "catalyst." A mixture of 1-butanol and methanol is said to be converted by the "catalyst" to a mixture of 2-ethyl-1-hexanol and 2-methyl-1-butanol.

Still other batch Guerbet reaction variations include water removal to improve yield and the use of an alkali metal hydroxide "catalyst" (U.S. Pat. No. 3,328,470), the use of an alkali metal alcoholate/boric acid ester "catalyst" (U.S. Pat. No. 2,861,110), and the addition of a nickel "catalyst" to the metal alkoxide (J. Am. Chem. Soc. 76, 52 (1953).

Octane demand has soared in recent years and the growth is likely to continue in the United States. For example, it has been estimated that clear pool octane demand has been increasing by 0.15 units/year in recent years. The addition of alcohols and ethers such as methanol, ethanol and methyl t-butyl ether to gasoline to improve octane number and/or improve the effect of gasoline combustion in internal combustion engines on the environment has been the subject of a number of recent publications.

Methanol is generally made from synthesis gas and ethanol can be made by carbonylation of methanol or more usually from agricultural products by fermentation. Higher alcohols can also result from the catalyzed conversion of synthesis gas. Methanol, while effective if used essentially pure for transportation fuel, is not a good additive for gasoline. Ethanol has shown promise as a gasoline additive, but isobutanol in particular is valuable as it can be dehydrated to isobutylene and reacted with methanol to form methyl t-butyl ether (MTBE) which is an excellent octane improver that can be easily blended into gasoline. Isobutanol is also an effective octane improver. The methyl ether of isopentanol (TAME) is also an excellent octane improver for gasoline. U.K. Patent Application GB 2,123,411 describes a process for making a mixture of octane improving ethers by synthesizing an alcohol mixture containing methanol, ethanol, and higher alcohols and dehydrating the higher alcohols and etherification.

Because of the large amount of methanol available and its problems as a gasoline additive, processes which convert methanol to effective gasoline additives are valuable. Well-known is the Mobil process for converting methanol to gasoline-range hydrocarbons over an aluminum-containing molecular sieve. Little work has been reported on effectively converting methanol to higher alcohols, in particular, isobutanol.

Now a material has been found which allows a continuous, vapor phase, catalytic Guerbet-type of condensation to be effected on a large variety of different alcohols, aldehydes and ethers and their mixtures. In particular, a catalyst effective in continuously converting a mixture of alcohols such as methanol and ethanol or a mixture of methanol, formaldehyde, and ethanol in a continuous vapor phase process to higher alcohols has been found which can produce a substantial percentage of isobutanol in the product. Such a catalyst allows the production of MTBE using exclusively synthesis gas as the source of carbon to the process.

SUMMARY OF THE INVENTION

The invention described herein is a continuous vapor phase process to convert a feed comprising a $C_2$ or higher alcohol, optionally in combination with one or more additional $C_1$ or higher alcohols to at least one higher molecular weight alcohol which comprises contacting said $C_2$ or higher alcohol, optionally in combination with one or more $C_1$ or higher alcohols in the vapor phase with a catalyst which is essentially magnesium oxide under condensation conditions to form a mixture containing said at least one or more higher molecular weight alcohol.

In another aspect, the invention described herein is a process for making methyl t-butyl ether from synthesis gas which comprises:

converting said synthesis gas to methanol;

converting part of said methanol to ethanol;

converting said ethanol and part of said methanol in a vapor phase, continuous process to a mixture rich in isobutanol over a condensation catalyst;

dehydrating said isobutanol to isobutene after separation from said mixture; and reacting said isobutene and said methanol to form said methyl t-butyl ether.

DESCRIPTION OF THE DRAWING

The Figure shows a simplified flow diagram for one embodiment of the invention in which synthesis gas is converted to MTBE using the continuous magnesium oxide-based, catalyzed, vapor phase condensation process.

DETAILED DESCRIPTION OF THE INVENTION

The $C_2$ or higher alcohols useful herein are $C_2$ to $C_{20}$ alcohols such as ethanol, a propanol, a butanol, a pentanol, a hexanol, a nonanol, a dodecanol, and the like. The only limitation on such alcohols is their ability to be vaporized and passed over the catalyst at a temperature low enough to avoid substantial decomposition. The $C_1$ or larger alcohols used in the invention include all of the above and methanol. The $C_1$ to $C_4$ aldehydes and $C_1$ to $C_6$ ethers generally include aldehydes and ethers such as formaldehyde, acetaldehyde, propionaldehyde, dimethyl ether, diethyl ether, methyl ethyl ether, methyl isopropyl ether, and the like. More preferred for the $C_2$ or higher and $C_1$ or higher alcohols are $C_1$ to $C_8$ alcohols including methanol, ethanol, propanol, n-butanol, 2-methylpropanol, n-pentanol, 3-methylbutanol, n-pentanol and the like. An especially preferred feed is a mixture of methanol, ethanol, and formaldehyde, a mixture of methanol and ethanol, a mixture of methanol, ethanol, and a propanol, or an effluent from a synthesis-gas-to-alcohols conversion process which contains methanol, ethanol and amounts of $C_{2+}$ alcohols. The feed to the process may in addition contain small amounts of one or more of methane, oxygen, nitrogen, hydrogen, carbon monoxide and carbon dioxide.

In general, after the feed is passed over the catalyst it will contain a mixture of alcohols at least one of which is of higher molecular weight than any of the starting alcohol or alcohols. For example, a mixture of methanol and ethanol and a mixture of methanol, formaldehyde and ethanol produces at least 1-propanol, and a mixture of methanol, ethanol, and 1-propanol produces at least isobutanol; a mixture of methanol and isopropanol produces at least 2-butanol; ethanol alone produces at least n-butanol; n-butanol alone produces at least 2-ethylhexanol, and propanol alone produces at least 2-methylpentanol. Small amounts of non-alcohol products such as aldehydes, ethers and ketones generally also occur in the product.

The magnesium oxide component useful in the catalyst herein described is essentially magnesium oxide. The magnesium oxide is present as more than about 80, more preferably more than about 90, and most preferably, more than about 95 wt. % of the total catalyst weight. The catalyst may also contain minor amounts of magnesium hydroxide, or alkaline materials such as a Period Group Ia or Group IIa compound including oxides and hydroxides. The magnesium oxide component is preferably of higher surface area, more preferably of surface area greater than about 25 sq m/g, and most preferably, of surface area above about 50 sq m/g, as measured by the BET method with nitrogen.

The magnesium oxide can be made by calcination of magnesium hydroxide or another magnesium compound such as magnesium carbonate or acetate. The preferred magnesium compound is magnesium hydroxide. The calcination temperature of the magnesium compound used should not be greatly in excess of the temperature needed to produce the oxide as the oxide can be produced in a less active form.

The catalyst may be used neat, but can be admixed with a diluent such as zirconia, titania, boria, alumina, and, particularly, a carbonaceous material such as charcoal and the like. Such diluents need not be completely inert and, indeed, it appears that the use of charcoal as a diluent improves certain of the condensation reactions described herein such as that of a mixture of methanol and ethanol, and a mixture of methanol, ethanol and a propanol. The diluent and the magnesium oxide component may be admixed in proportions of from 100 wt. % magnesium oxide component and no diluent to about 10 wt. % magnesium oxide component and about 90 wt. % diluent. More preferably, the proportions may vary between about 80 wt. % magnesium oxide component and about 20 wt. % diluent to about 20 wt. % magnesium oxide component and about 80 wt. % diluent.

The magnesium oxide component may in addition be supported on such supports as titania, alumina, silica, boria, zirconia, and a carbonaceous material such as charcoal and the like, by impregnation or otherwise. Magnesium oxide component/support wt. % ratios are generally the same as described above for catalysts wherein the magnesium oxide component is admixed with a diluent.

Use of a carrier gas mixed with the feed to the process can be advantageous. Such materials as hydrogen, carbon monoxide, carbon dioxide, a hydrocarbon, and inert gases such nitrogen, argon, and the like may be used to improve the condensation reaction. The use of hydrogen in the process can improve selectivity and, if used, is generally employed in a hydrogen/feed ratio of from about 20:1 to about 1:1, more preferably, about from 10:1 to about 1:1.

The catalyst, with or without a carrier gas added to the feed, can be used in a fixed bed, ebullated bed, fluidized bed, or other type of vapor phase process. A copper-walled reactor has been found to be beneficial. In general, the temperature range useful in carrying out the condensation reaction described herein runs between about 300° and about 700° C., more preferably, between about 300° and about 500° C., and most preferably, between about 325° and about 450° C. The range of total reactor pressure useful in this invention runs between subatmospheric and about 1000 psig, more preferably, between subatmospheric and about 600 psig, and most preferably, subatmospheric to about 500 psig. Useful weight hour space velocities run between about 0.05 and about 50 hr$^{-1}$, and more preferably, between about 0.05 and about 10 hr$^{-1}$, based upon the magnesium oxide component in the catalyst.

A particularly useful process which may be carried out employing the condensation reaction is the production of MTBE from synthesis gas as the sole carbon source. In such a process, synthesis gas is converted to methanol which is converted, for example, by carbonylation to ethanol. The ethanol is then condensed using a condensation catalyst such as the one disclosed herein with methanol to form a mixture rich in isobutanol.

Other catalysts may also be used. The isobutanol may then be separated from the mixture, dehydrated, and reacted with additional methanol to form MTBE. One possible process of accomplishing production of MTBE is set out below to illustrate this use. The description of such process is not meant to limit the invention in any way.

In the Figure, synthesis gas ($H_2O$ and CO) is added to gas separation section 2 where the synthesis gas is separated into a CO rich and a CO depleted fraction exiting through lines 3 and lines 4 respectively. The separation can be effected in any one of several ways including, but not limited to, pressure swing absorption, membrane removal of hydrogen, cryogenic separation, or a chemical separation such as that employing the COSORB technology, as may be understood by one skilled in the art. The CO depleted stream (line 4) goes to methanol synthesis section 5 where any of the commercial technologies to covert synthesis gas (especially hydrogen-rich synthesis gas) to methanol can be used. Methanol synthesis produces methanol exiting through line 6 and a hydrogen-rich purge stream 7. A portion of the methanol exiting through lines 6 goes into line 6' and is reacted with the CO rich stream of line 3 in carbonylation section 8 using any of the available carbonylation technologies to produce acetic acid or methyl acetate as may be understood by one skilled in the art. The latter acid or ester exits through line 9 to hydrogenolysis section 10 and is reacted with hydrogen entering hydrogenolysis section 10 through line 7 to form ethanol or a mixture of methanol and ethanol which exits through line 11. It is preferred to combine carbonylation and hydrogenolysis in a single step. The methanol and ethanol in line 11 are mixed with additional methanol from methanol synthesis section 5 through lines 6, 12 and 13 in catalytic condensation section 14 which contains a magnesium oxide-based catalyst. Catalytic condensation section 14 is generally run at a high methanol to ethanol ratio to suppress formation of n-butanol. The effluent from catalytic alcohol condensation section 14 is transferred through line 15 to separation section 16 where it can be fractionated. The isobutanol and isopentanol portion of the fractionation in section 16 is sent via line 17 to dehydration section 18 where the alcohols are dehydrated using a convention alcohol dehydration technology, and the olefins produced are transferred through line 19 to MTBE formation section 20. MTBE formation section 20 uses methanol for addition to the olefins which comes to section 20 through line 12. MTBE and the methyl ether of isopentanol (TAME) are removed through line 21. Other alcohols than isobutanol and isopentanol which are produced in catalytic alcohol condensation section 14 are separated during the fractionation in separation section 16 and recycled to the feed of section 14 through line 22.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

General

All catalysts were evaluated in a fixed bed, continuous, down flow, stainless steel reactor. For some of the studies the stainless steel reactor was equipped with either a quartz or a copper liner. The catalyst was ground to 12/20 mesh size and physically mixed with bed diluent, charcoal, or alumina of the same mesh size. The catalyst bed was centered in the reactor with an inert alumina balls baffle above and below it for improved heat transfer. The alumina balls were kept at a lower temperature than the catalyst bed. The unit was pressured with helium unless otherwise noted and the catalyst brought to reaction temperature in flowing helium, at which time the alcohol was introduced via a Ruska pump.

Products were analyzed by three gas chromatographic systems. The fixed gases, CO and $CO_2$ along with $CH_4$ were analyzed by an on-line Hewlett-Packard 5730 gas chromatograph equipped with a thermal conductivity detector and a Chromosorb 106 packed column. Analysis was accomplished by using an external standard calibrated for CO, $CO_2$ and $CH_4$. The noncondensible light gases, $C_1$–$C_6$, were analyzed off-line using a flame ionization detector and a 6 ft N-octane Porosil C column. The peaks were identified and measured by matching retention times with an external standard containing $C_1$–$C_6$ hydrocarbons.

The condensible materials were collected in a bomb and analyzed with a flame ionization detector equipped with a 30 m capillary column of fused silica containing RSL 160 liquid phases. Peaks were identified by matching retention times of known alcohols, aldehydes, esters, ketones, olefins and paraffins. Many smaller peaks were not identified. The results are expressed in relative weight percents.

The condensible liquids were also measured on a Hewlett-Packard 5730 gas chromatograph equipped with a thermal conductivity detector. A 6 ft × ⅛ in Poropak QS column, 80/100 mesh particles, was used. This system gave semiquantitative results for water, $C_1$–$C_5$ alcohols, and some of the lower molecular weight aldehydes, ketones and esters.

EXAMPLE 1

Magnesium oxide was prepared from 25 kg of commercially available magnesium hydroxide (VWR Scientific, Inc. reagent grade powder) by first mixing with 2000 g of distilled water and extruding the mass through a ⅛ in die plate. The extrudate was dried overnight at 120° C. and calcined first at 300° C. for 1 hr and then 450° C. for 12 nr. The resulting MgO having a BET surface area of 29 $m^2$/g was used for Examples 2–6.

EXAMPLE 2

A 3.23 g (5 ml) quantity of magnesium oxide was mixed with 29 ml of charcoal supplied by Sargent-Welch as the catalyst. A 3/1 methanol to ethanol reactor feed and a copper lined reactor were used for this Example.

TABLE 1

| | |
|---|---|
| Temperature °F. | 800 |
| Pressure | 150 psig |
| Helium Flow | 0.099 $ft^3$/hr |
| WHSV ($hr^{-1}$) | 2.5 |
| Wt % Methanol Converted | 22.4 |
| Wt % Ethanol Converted | 99.5 |
| Wt % Selectivity (Water-Free Basis) of Products | |
| 1-Propanol | 8.3 |
| Isobutanol | 31.6 |
| 1-Butanol | 0 |
| t-Butanol | 5.4 |

TABLE 1-continued

| | |
|---|---|
| CO + CO₂ | 22.1 |
| Methane | 5.4 |
| Ethane + Ethylene | 3.1 |
| Propane | 6.5 |
| Propylene | 1.2 |
| C₄ Hydrocarbons | 4.3 |
| C₅ + Hydrocarbons | 2.1 |
| Acetaldehyde | 0 |
| Other | 10.0 |

EXAMPLE 3

Alcohol conversion is a function of space velocity and diluent character for the reaction of ethanol and methanol was studied and the results are shown in Tables 2, 3, and 4 below. A 3/1 methanol to ethanol reactor feed composition was used.

TABLE 2

Conversion as a Function of Space Velocity and Bed Diluent in a Copper Reactor

| WHSV (hr⁻¹) | % Methanol Converted | | | % Ethanol Converted | | |
|---|---|---|---|---|---|---|
| | Neat | Charcoal | Alumina | Neat | Charcoal | Alumina |
| 0.6 | 9 | 41 | — | 35 | 100 | — |
| 2.5 | 3 | 22 | — | 21 | 99 | — |
| 4.1 | — | 3 | — | — | 43 | — |

TABLE 3

Conversion as a Function of Space Velocity and Bed Diluent in a Stainless Steel Reactor

| WHSV (hr⁻¹) | % Methanol Converted | | | % Ethanol Converted | | |
|---|---|---|---|---|---|---|
| | Neat | Charcoal | Alumina | Neat | Charcoal | Alumina |
| 0.6 | 32 | 99 | — | 54 | 99 | — |
| 2.5 | 9 | 82 | 32 | 25 | 100 | 59 |

TABLE 4

Conversion as a Function of Space Velocity and Bed Diluent in a Quartz Reactor

| WHSV (hr⁻¹) | % Methanol Converted | | | % Ethanol Converted | | |
|---|---|---|---|---|---|---|
| | Neat | Charcoal | Alumina | Neat | Charcoal | Alumina |
| 0.6 | 23 | 5 | — | 63 | 13 | — |
| 2.5 | 12 | 1 | — | 37 | 4 | — |

EXAMPLE 4

The effect of a bed diluent on product distribution in a cooper-lined reactor for the reaction of ethanol and methanol is given in Table 5 below. A 3/1 methanol to ethanol reactor fed was used.

TABLE 5

Effect of Bed Diluent on Product Selectivity in a Copper Reactor

| Bed Diluent | None | Charcoal |
|---|---|---|
| Temperature °F. | 800 | 800 |
| WHSV (hr⁻¹) | 2.5 | 2.5 |
| Wt % Methanol Converted | 3.3 | 22.4 |
| Wt % Ethanol Converted | 21.4 | 99.5 |
| Wt % Selectivity (Water-Free Basis) of Products | | |
| 1-Propanol | 35.4 | 8.3 |
| Isobutanol | 2.5 | 31.6 |
| 1-Butanol | | |
| t-Butanol | | 5.4 |
| CO + CO₂ | 14.2 | 22.1 |
| Methane | 1.5 | 5.4 |
| Ethane + Ethylene | 3.1 | 3.1 |
| Propane | 0 | 6.5 |
| Propylene | 0.7 | 1.2 |

TABLE 5-continued

Effect of Bed Diluent on Product Selectivity in a Copper Reactor

| Bed Diluent | None | Charcoal |
|---|---|---|
| C₄ Hydrocarbons | 0 | 4.3 |
| C₅⁺ Hydrocarbons | 0 | 2.1 |
| Acetaldehyde | 17.8 | 0 |
| Other | 17.5 | 10.0 |

EXAMPLE 5

The effect of a bed diluent on product distribution on the reaction of ethanol and methanol in a quartz reactor is given below in Table 6. A 3/1 methanol to ethanol reactor feed was used.

TABLE 6

Effect of Bed Diluent on Product Selectivity in a Quartz Reactor

| Bed Diluent | None | Charcoal |
|---|---|---|
| Temperature °F. | 800 | 800 |
| WHSV (hr⁻¹) | 0.6 | 0.6 |
| Wt % Methanol Converted | 23.5 | 5.3 |
| Wt % Ethanol Converted | 62.5 | 13.4 |
| Wt % Selectivity (Water-Free Basis) of Products | | |
| 1-Propanol | 0 | 0 |
| Isobutanol | 0 | 0 |
| 1-Butanol | 0 | 0 |
| t-Butanol | 0 | 0 |
| CO + CO₂ | 41.8 | 29.6 |
| Methane | 4.0 | 5.9 |
| Ethane + Ethylene | 2.2 | 3.1 |
| Propane | 0.2 | 9.3 |
| Propylene | 0.6 | 0 |
| C₄ Hydrocarbons | 0.1 | 2.3 |
| C₅⁺ Hydrocarbons | 0.1 | 0 |
| Acetaldehyde | 49.5 | 49.8 |
| Other | 1.5 | 0 |

EXAMPLE 6

The effect of differing bed diluents on the reaction of methanol and ethanol in a stainless steel reactor is given below in Table 7. A 3/1 methanol to ethanol reactor fed was used.

TABLE 7

Effect of Bed Diluent on Product Selectivity in a Stainless Steel Reactor

| Bed Diluent | None | Charcoal | Alumina |
|---|---|---|---|
| Temperature °F. | 800 | 800 | 800 |
| WHSV (hr⁻¹) | 2.5 | 2.5 | 2.5 |
| Wt % Methanol Converted | 7.6 | 90.6 | 29.0 |
| Wt % Ethanol Converted | 20.4 | 99.1 | 54.6 |
| Wt % Selectivity (Water-Free Basis) of Products | | | |
| 1-Propanol | 21.1 | 0.1 | 3.0 |
| Isobutanol | 0 | 0.8 | 0 |
| 1-Butanol | 0 | 0 | 0 |
| t-Butanol | 0 | 0 | 0 |
| CO + CO₂ | 35.8 | 67.7 | 57.6 |
| Methane | 10.2 | 12.6 | 6.9 |
| Ethane + Ethylene | 5.6 | 5.4 | 2.7 |
| Propane | 0.1 | 2.0 | 0.3 |
| Propylene | 0.8 | 3.4 | 2.5 |
| C₄ Hydrocarbons | 0 | 2.5 | 0.4 |
| C₅⁺ Hydrocarbons | 0.2 | 1.8 | 0.5 |
| Acetaldehyde | 9.4 | 0.3 | 18.2 |
| Other | 16.6 | 3.3 | 7.7 |

EXAMPLE 7

A 500 g portion of magnesium hydroxide powder supplied by Sargent-Welsh was placed in a beaker, treated with water to make a thick paste, and then dried at 130° C. A first portion of it was calcined at 450° C. for 12 hr and a second portion was calcined at 538° C. for 12 hr. The latter material shows a pore volume of 0.9793 cc/g, an average pore radius of 197Å, and a BET (nitrogen) surface area of 90 m$^2$/g. Both calcination products were crushed and sieved to 18/40 mesh granules.

EXAMPLE 8

Both MgO products of Example 7 were loaded into a quartz reactor, and a 3/1 methanol to ethanol feed passed over the catalyst for 1 hr at 450° C. The results are set out below in Table 8.

TABLE 8

Effect of Calcination Temperature on Product Distribution

| Component | 538° C. Product (%) | 450° C. Product (%) |
|---|---|---|
| acetaldehyde | 0.75 | * |
| propionaldehyde | 0.59 | * |
| isobutyraldehyde + acetone | 0.47 | 1.48 |
| methanol | 50.6 | 36.11 |
| ethanol | 17.4 | 3.66 |
| n-propanol | 10.3 | 5.68 |
| isobutanol | 7.63 | 29.4 |
| allyl alcohol | 1.0 | * |
| n-butanol | 1.78 | 0.62 |
| 2-Me-1-butanol | 3.13 | 6.35 |

*not measured

EXAMPLE 9

A 73.58 g portion of Al(NO$_3$)$_3$·9H$_2$O was dissolved in 140 g of water. A 130.25 g portion of magnesium hydroxide was slowly added to the solution until a solid paste was formed. Additional water and the remaining hydroxide were added until the thick paste was again formed. The paste was dried at 121° C. and calcined 12 hr at 538° C. The product catalyst contains about 10 wt. % aluminum oxide.

EXAMPLE 10

A 5/1 methyl alcohol/diethyl ether mixture (0.0126 ml/min of mixture, 6 ml/min of nitrogen) was passed over 9.4 ml of catalyst in a quartz reactor at 430° C. and ambient pressure of 140 min giving 0.94 g of liquid product in a dry ice-isopropanol trap. The product distribution is given below in Table 9.

TABLE 9

| Liquid Product Component | Wt. % |
|---|---|
| methyl ether | 5.79 |
| methyl ethyl ether | 3.62 |
| diethyl ether | 41.7 |
| methyl n-propyl ether | 1.53 |
| methyl isobutyl ether | 2.41 |
| propionaldehyde | 0.67 |
| isobutyraldehyde + acetone | 0.84 |
| methanol | 31.4 |
| ethanol | 4.51 |
| n-propanol | 2.21 |
| isobutanol | 4.62 |
| 2-Me-1-butanol | 0.27 |

EXAMPLE 11

A 2/1 methanol/n-butanol mixture (0.126 ml/min of mixture, 6 ml/min of nitrogen) was passed over the 538° C. calcined MgO catalyst of Example 7 at 425° C. and ambient pressure for 60 min giving 0.77 g of liquid product in a dry ice-isopropanol trap. The product distribution is shown in Table 10 below:

TABLE 10

| Liquid Product Component | Wt. % |
|---|---|
| methyl alcohol | 24.7 |
| isopropanol | 0.88 |
| n-butanol | 45.8 |
| 2-Me-1-butanol | 19.3 |
| 2-Me-1-pentanol | 1.54 |

EXAMPLE 12

Ethanol (0.0126 ml/min, 6 ml/min of nitrogen) was passed over the 538° C. calcined magnesium oxide of Example 7 at 425° C. and ambient pressure for 105 min giving 0.82 g of liquid product trapped in a dry ice-isopropanol trap. The product distribution is shown below in Table 11.

TABLE 11

| Liquid Product Component | Wt. % |
|---|---|
| acetaldehyde | 1.4 |
| propionaldehyde | 0.6 |
| i-butyraldehyde + acetone | 0.78 |
| n-butyraldehyde | 0.6 |
| methanol | 1.7 |
| 2-butanone | 0.87 |
| 2-propanol | 2.4 |
| ethanol | 39.6 |
| methyl vinyl ketone | 0.9 |
| 2-pentanone | 1.2 |
| 2-butanol | 1.0 |
| n-propanol | 1.0 |
| crotonaldehyde | 0.67 |
| allyl alcohol | 1.59 |
| mesityl oxide | 0.48 |
| n-butanol | 14.8 |
| 2-methyl-1-butanol | 0.78 |

EXAMPLE 13

A 5/1/1 methanol, ethanol, and 1-propanol mixture (0.0126 ml/min, 6 ml/min of nitrogen) was passed over the 538° C. calcined magnesium oxide of Example 7 at 425° C. and ambient pressure for 120 min giving 1.36 g of liquid product trapped in a dry ice-isopropanol trap. The product distribution is shown below in Table 12.

TABLE 12

| Liquid Product Component | Wt. % |
|---|---|
| acetaldehyde | 0.67 |
| methyl n-propyl ether | 0.98 |
| ethyl n-butyl ether | 1.17 |
| isobutyraldehyde + acetone | 1.35 |
| methanol | 37.4 |
| ethanol | 6.74 |
| i-propanol | 13.2 |
| i-butanol | 24.1 |
| 2-Me-1-butanol | 2.04 |
| 2-Me-1-pentanol | 2.19 |

What is claimed is:

1. A continuous vapor phase process to convert a feed comprising one or more C$_2$ or higher alcohol in combination with methanol to at least one higher molecular weight alcohol which comprises contacting said one or more C$_2$ or higher alcohol in combination with methanol in the vapor phase with magnesium oxide, said magnesium oxide of surface area above about 25 sq m/g and made by heating magnesium hydroxide in the temperature range from above its decomposition temperature to about 538° C., under condensation conditions to form a mixture containing said at least one higher molecular weight alcohol.

2. The process of claim 1 wherein said magnesium oxide is admixed with charcoal.

3. The process of claim 1 wherein said feed comprises a mixture of methanol and ethanol, a mixture of methanol, formaldehyde and ethanol, a mixture of methanol, ethanol and acetaldehyde, or a mixture of methanol and a propanol.

4. The process of claim 1 wherein said feed comprises a mixture of methanol and ethanol, a mixture of methanol, formaldehyde and ethanol, or a mixture of methanol, ethanol and a propanol.

5. The process of claim 2 wherein said process is carried out in the presence of a copper surface.

6. A continuous vapor phase process to convert a feed containing at least methanol and ethanol to at least one alcohol of higher molecular weight than ethanol which comprises contacting said feed with magnesium oxide, said magnesium oxide of surface area above about 25 sq m/g and made by heating magnesium hydroxide in the temperature range from above its decomposition temperature to about 538° C., under condensation conditions to form a mixture containing said at least one alcohol of higher molecular weight.

7. The process of claim 6 wherein said magnesium oxide is admixed with charcoal.

8. The process of claim 6 wherein said at least one alcohol of higher molecular weight is isobutanol.

9. The process of claim 6 wherein said feed additionally contains a $C_1$ to $C_4$ aldehyde.

10. The process of claim 6 wherein said feed additionally contains a $C_1$ to $C_6$ ether.

11. The process of claim 6 wherein said feed additionally contains a $C_1$ to $C_4$ aldehyde and a $C_1$ to $C_6$ ether.

* * * * *